United States Patent [19]
Pilling

[11] Patent Number: 5,522,839
[45] Date of Patent: Jun. 4, 1996

[54] DISSECTING FORCEPS

[75] Inventor: William H. Pilling, North Wales, Pa.

[73] Assignee: Pilling Weck Incorporated, Fort Washington, Pa.

[21] Appl. No.: 304,094

[22] Filed: Sep. 9, 1994

[51] Int. Cl.⁶ .................................................. A61B 17/28
[52] U.S. Cl. ........................ 606/207; 600/204; 600/219; 606/198; 606/205
[58] Field of Search ................................. 606/170, 174, 606/205, 207, 210, 198; 600/204, 219; 128/751

[56] References Cited

U.S. PATENT DOCUMENTS 5,201,752  4/1993  Brown et al. ............................ 606/190
5,352,235  10/1994  Koros et al. ............................. 606/174

OTHER PUBLICATIONS

Jarit Laparoscopic Cholecystectomy Instrumentation Star 2000 Series Catalog, 1991, pp. 2–3.

*Primary Examiner*—Michael H. Thaler
*Assistant Examiner*—Patrick W. Rasche
*Attorney, Agent, or Firm*—Howson and Howson

[57] ABSTRACT

An improved dissecting forceps comprises an elongated shaft which fits closely within the lumen of a trocar. A smaller rod extends beyond the distal end of the shaft. A pair of jaws at the distal end of the rod are hinged so that they are movable relative to each other, and meet at a surface when closed. The jaws have bumps at their proximal ends which extend away from the surface at which the jaws meet when closed. A control mechanism located at the proximal end of the shaft causes at least one of the jaws to move relative to the other jaw. Elements of connective tissue are separated when the jaws are spread apart after having been inserted between the tissue. The bumps prevent the tissue from sliding along the jaws in the proximal direction as the jaws are spread apart.

6 Claims, 2 Drawing Sheets

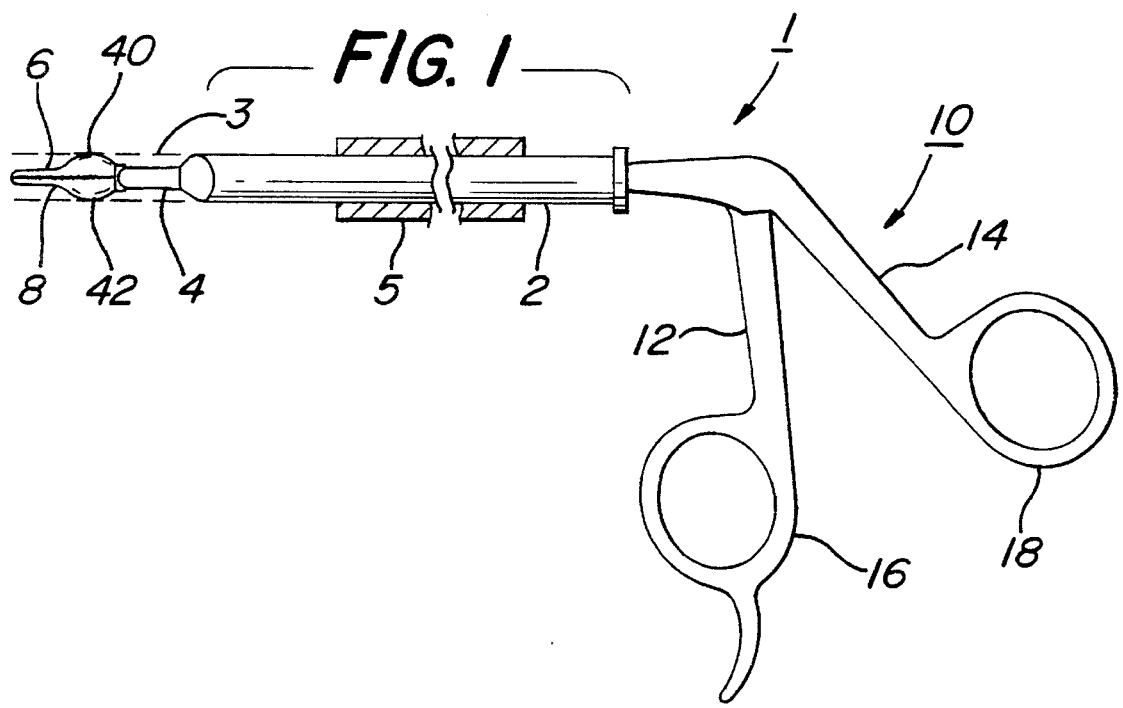
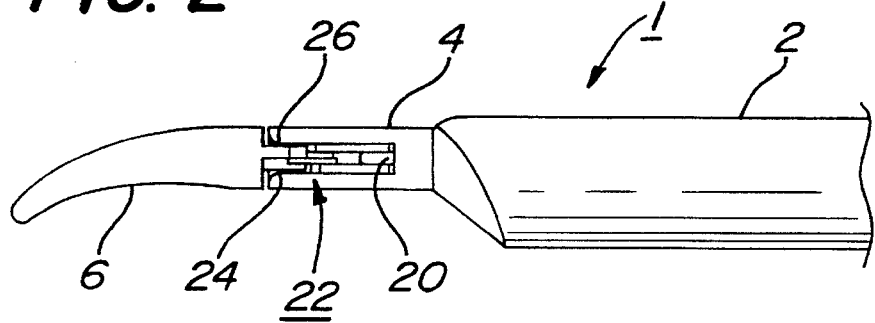
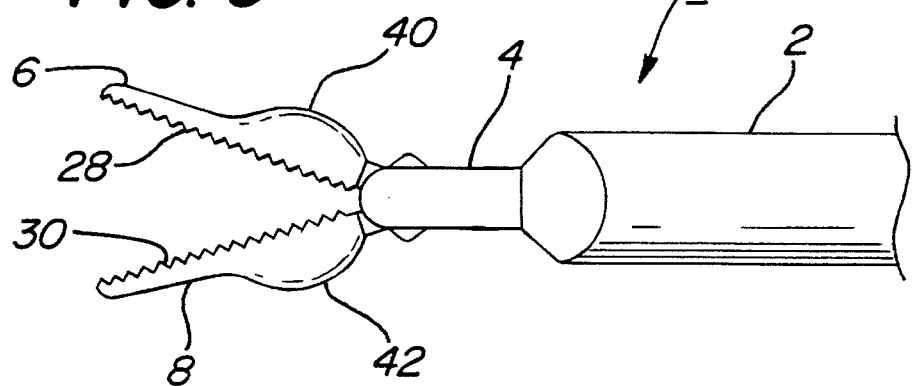

DISSECTING FORCEPS

BRIEF SUMMARY OF THE INVENTION

This invention relates to dissecting forceps for use in laparoscopic surgery. It is specifically concerned with an improved forceps which more effectively separates elements of connective tissue while closely fitting within the lumen of a cannula.

Elements of connective tissue are routinely separated in laparoscopic surgery. For example, in gall bladder operations, it is often necessary to clear the cystic duct and the cystic artery from each other and from the surrounding tissue so that clips can be placed on both.

This separating procedure is carried out as part of an endoscopic surgical procedure in which openings are made in the wall of the patient's abdomen by means of trocars. Each trocar is part of a trocar/cannula combination comprising a tube (the cannula), and a cutting device (the trocar) having a sharp cutting end and removably extending through the tube. When the trocar is removed, the cannula is left in place to maintain an opening for the duration of the surgical procedure. A specially designed dissecting forceps, having a shaft which closely conforms to the interior wall of the cannula, is introduced through the cannula into the patient's abdominal cavity, which has been enlarged by inflation with carbon dioxide through another cannula. The close fit of the shaft of the forceps with the interior wall of the cannula prevents the carbon dioxide from escaping rapidly. The operation is observed by the surgeon and assistants on a television monitor which displays the image picked up by a miniature television camera attached to a telescope introduced through still another cannula.

Conventional dissecting forceps of the kind used in laparoscopic surgery have an elongated, straight shaft which fits closely within the lumen of a cannula A pair of jaws is provided at the distal end of the shaft. A control mechanism at the proximal end of the shaft allows an operator to move the jaws relative to each other. The jaws can be used in the conventional manner for grasping and extracting tissue. The jaws can also be inserted between elements of connective tissue in the closed position, and are subsequently opened to spread the tissue apart. When the jaws are opened, the tissue tends to slide in the proximal direction along the jaws, and when this sliding occurs, the tissue is not separated adequately.

The principal object of this invention is therefore to provide a dissecting forceps for laparoscopic surgery, which more effectively separates elements of connective tissue and avoids the aforementioned problem of proximal sliding. Another object of this invention is to provide a dissecting forceps which is simple and inexpensive to manufacture. It is also an object of this invention to promote ease of use, durability, and reliability.

The dissecting forceps in accordance with the invention comprises an elongated shaft which has a diameter sufficient to fit closely within the lumen of a cannula. This prevents inflation gas from escaping out of a patient's abdomen when the cannula extends through the abdominal wall and the shaft is in place within the lumen of the cannula. An elongated rod with a diameter less than that of the shaft extends distally beyond the distal end of the shaft. A pair of jaws at the distal end of the rod are movable relative to each other and meet at a surface when closed. The jaws have bumps at their proximal ends which extend away from the surface at which the jaws meet when closed. A control mechanism located at the proximal end of the shaft causes at least one of the jaws to move relative to the other jaw. Elements of connective tissue are separated when the jaws are spread apart after having been inserted between the elements of tissue. The bumps prevent the tissue from sliding along the jaws in the proximal direction as the jaws are spread apart.

BRIEF DESCRIPTION OF THE DRAWINGS

FIG. 1 is a side elevational view of the dissecting forceps in accordance with the invention;

FIG. 2 is a fragmentary top plan view showing the distal end portion of the dissecting forceps of FIG. 1, including the jaws, the rod, part of the shaft, and part of the control mechanism for opening and closing the jaws;

FIG. 3 is a fragmentary side elevational view of the distal end of the dissecting forceps of FIG. 2 showing the jaws in the open position;

DETAILED DESCRIPTION

Figure 4:
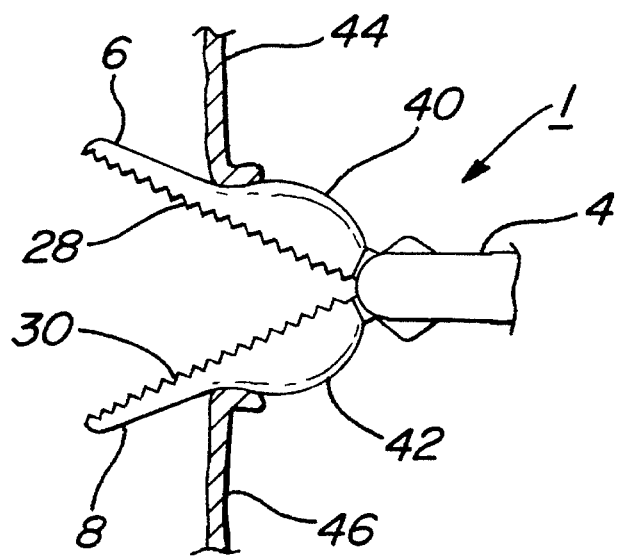
FIG. 4 is a fragmentary side elevational view of the distal end of the dissecting forceps of FIG. 2 showing the jaws in the open position, separating elements of connective tissue.

The dissecting forceps 1, shown in FIGS. 1, 2, and 3, comprises an elongated, hollow shaft 2 having a circular, cylindrical outer wall. The diameter of the shaft 2 is such that it fits closely within, and is slidable through, the lumen of a cannula 5. The cannula 5 maintains an opening in the patient's abdomen for the duration of the surgical procedure. Because the outer surface of the shaft 2 fits closely within the cannula 5, the escape of inflation gas from the patient's abdomen is retarded.

An elongated, hollow rod 4, with a diameter less than that of the shaft 2, is rigidly connected to the shaft 2 and protrudes distally beyond the distal end of the shaft 2.

Jaws 6 and 8, shown in FIGS. 1, 2, 3, and 4 at the distal end of the rod, are movable relative to each other so that they meet at a surface when closed. The jaws 6 and 8 are preferably curved in the surface on which the jaws meet when closed. The curvature of the jaws makes it easier for the surgeon to reach various tissues to be separated, especially in gall bladder surgery. At least when the jaws are closed, the tips of the jaws are within the confines of an imaginary cylinder 3 (FIG. 1) which is an extension of the cylindrical outer wall of shaft 2. Thus the rod 4 and jaws 6 and 8 are located entirely within the imaginary cylinder. The rod 4 is parallel to the shaft 2 and is offset so that it is adjacent to one side of the imaginary cylinder. The curvature of the jaws 6 and 8 is such that the tips of the jaws 6 and 8 are adjacent to the opposite side of the imaginary cylinder. The rod 4 and jaws 6 and 8, therefore, do not prevent the passage of the shaft 2 through the cannula.

A handle 10 shown in FIG. 1 is located at the proximal end of the shaft 2. The handle 10 has two arms 12 and 14, each having a loop 16 and 18. An operator inserts a finger into each loop 16 and 18 to manipulate the forceps 1 in scissor-like fashion.

One arm 12 is movable relative the other arm 14, which remains rigid. Moving arm 12 away from arm 14 pushes a bar 20, shown in FIG. 2, toward the distal end of the forceps 1. The bar 20 is attached to a hinge 22 having two elements 24 and 26. Element 24 is connected to jaw 6 and element 26 is connected to jaw 8. When arm 12 pushes the bar 20 distally, the hinge 22 opens the jaws 6 and 8. When arm 12 pulls the bar 22 proximally, the hinge 22 closes the jaws 6 and 8.

In the illustrated embodiment of the invention, the jaws 6 and 8 have serrated edges 28 and 30. This enables the forceps 1 to be used to grip tissue as well as to separate tissue.

Figure 5:
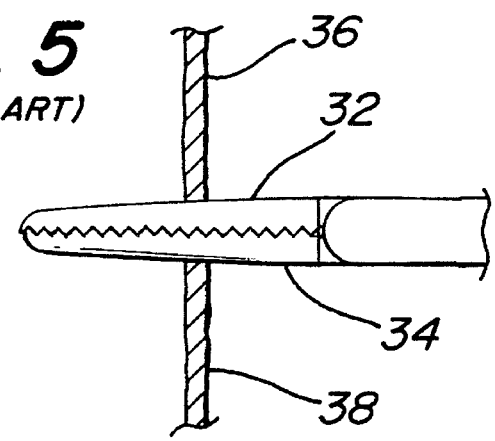
FIG. 5 is a fragmentary side elevational view showing the distal end of a dissecting forceps of the prior art, with its jaws in the closed position between elements of connective tissue.
Figure 6:
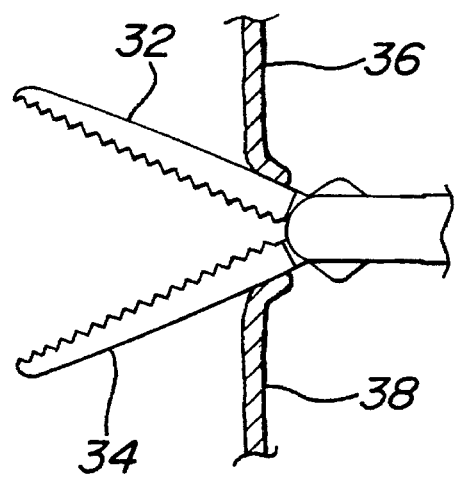
FIG. 6 is a fragmentary side elevational view showing the distal end of the dissecting forceps of FIG. 5, with the jaws in an open condition.

A dissecting forceps of the prior art, shown in FIGS. 5 and 6, also has a pair of jaws 32 and 34. The conventional jaws 32 and 34 are inserted between elements of connective tissue 36 and 38 as shown in FIG. 5. Opening the jaws 32 and 34 subsequent to insertion between elements of connective tissue 36 and 38 spreads the tissue 36 and 38 apart as shown in FIG. 6. However, when the jaws 32 and 34 are opened the tissue 36 and 38 tends to slide in the proximal direction along the outside portion of the jaws 32 and 34. This prevents the elements of tissue 36 and 38 from being separated adequately. The tissue elements 32 and 34 have a tendency to slide proximally as shown in FIG. 6.

In the improved forceps 1, shown in FIGS. 1, 2, 3, and 4, bumps 40 and 42 are provided on the proximal ends of the jaws 6 and 8. These bumps extend away from the surface at which the jaws meet when closed, but do not extend beyond the cylinder 3. Thus, the bumps 40 and 42 do not prevent the passage of the jaws 6 and 8 through the cannula.

The improved forceps 1 are operated in substantially the same manner as conventional dissecting forceps. Opening the jaws 6 and 8 after insertion between elements of connective tissue spreads the tissue elements 44 and 46 apart as shown in FIG. 4. Tissue elements 44 and 46 contact the bumps 40 and 42 after sliding a short distance along the outer portions of the jaws 6 and 8o The bumps 40 and 42 prevent the tissue elements 44 and 46 from continuing along the outer portion of the jaw 6 and 8.

The jaws 6 and 8 are tapered at their distal ends. This makes it easier to insert the jaws 6 and 8 between connective tissue elements 44 and 46. The proximal ends of the bumps 40 and 42 are preferably flush with the distal end of the rod 4. This prevents the bumps 40 and 42 from catching on tissue 44 and 46 when the forceps 1 is removed from the abdomen.

The improved dissecting forceps 1 more effectively separates elements of connective tissue 44 and 46 and closely fits within the lumen of a trocar. The improvement does not substantially increase the cost of manufacturing the forceps.

Various changes may be made to the described embodiments. For example, scissor blades may be substituted for the serrated edges 28 and 30 of the jaws 6 and 8. This would enable the forceps 1 to cut tissue rather than to clamp it. The jaws 6 and 8 do not have to be curved, and may instead extend substantially straight and parallel to the rod 4.

Still other modifications, which will occur to persons skilled in the art, may be made without departing from the scope of the invention as defined in the following claims.

I claim:

1. Dissecting forceps for use with a cannula in laparoscopic surgery, comprising:

an elongated shaft having distal and proximal ends, said shaft having an outer wall in the shade of a cylinder with a diameter sufficient to fit closely within the lumen of a cannula so that inflation gas will not readily escape from the abdomen of a patient when the cannula extends through the abdominal wall and said shaft is in place within the lumen of the cannula;

a rod with an outer diameter less than that of the shaft and having distal and proximal ends, said rod being connected to the shaft and extending, in the direction of the length of the shaft, beyond the distal end of the shaft;

a pair of jaws at the distal end of the rod, said jaws having opposed gripping surfaces and being mounted for movement relative to each other so that their gripping surfaces can move apart to receive tissue and come together to clamp tissue between them, and, when their gripping surfaces are together, defining an outer surface having distal and proximal ends, said outer surface having a first region extending from the distal end of said outer surface to an intermediate location between the distal and proximal ends of said outer surface, and a second region extending from said intermediate location to the proximal end of said outer surface, said outer surface being narrow and elongated substantially throughout said first region and having a bulbous shape substantially throughout said second region, with a transition, at said intermediate location between the narrow, elongated outer surface and the bulbous shaped outer surface, the bulbous shaped outer surface having a dimension transverse to the length of the rod which is greater than the diameter outer of the rod, and tapering toward the rod at the proximal end of the outer surface of the jaws; manipulable means at said proximal end of the shaft; and means connecting the manipulable means with at least one of the jaws to transmit both opening and closing forces from the manipulable means to the jaws;

whereby elements of connective tissue are separated when the jaws are spread apart after the first region of the outer surface of the jaws is inserted between said elements of tissue, and said bulbous shaped outer surface in the second region prevents said tissue elements from sliding proximally along the jaws as said jaws are spread apart.

2. Dissecting forceps according to claim 1 in which the rod is connected to the distal end of the shaft at a location such that the jaws are located entirely within an imaginary extension of said cylinder when the jaws are closed.

3. Dissecting forceps according to claim 2 wherein the imaginary extension of the cylinder has first and second opposite sides, the rod extends parallel to the shaft and adjacent to said first side of the imaginary extension, and the jaws are curved so that the distal end of the jaws is adjacent to said second side of the imaginary extension.

4. Dissecting forceps according to claim 3 in which, when the jaws are closed, the bulbous shaped outer surface of the jaws extends substantially completely across the imaginary extension of said cylinder.

5. Dissecting forceps according to claim 1 in which the diameter of the shaft is such that it can fit closely within the lumen of a 10 mm cannula.

6. Dissecting forceps according to claim 1 in which, when the jaws are closed, the bulbous shaped outer surface of the jaws extends substantially completely across the imaginary extension of said cylinder.

* * * * *